US012708788B2

(12) United States Patent
Jacofsky et al.

(10) Patent No.: US 12,708,788 B2
(45) Date of Patent: Aug. 18, 2026

(54) INTERNAL COLD PLASMA SYSTEM

(71) Applicant: Plasmology4, Inc., Scottsdale, AZ (US)

(72) Inventors: Marc C. Jacofsky, Phoenix, AZ (US); David J. Jacofsky, Peoria, AZ (US); Steven A. Myers, Scottsdale, AZ (US); Jeffrey I. Meyers, Phoenix, AZ (US)

(73) Assignee: Plasmology4, Inc., Scottsdale, AZ (US)

(*) Notice: Subject to any disclaimer, the term of this patent is extended or adjusted under 35 U.S.C. 154(b) by 708 days.

(21) Appl. No.: 18/155,493

(22) Filed: Jan. 17, 2023

(65) Prior Publication Data

US 2023/0166121 A1 Jun. 1, 2023

Related U.S. Application Data

(62) Division of application No. 15/177,188, filed on Jun. 8, 2016, now abandoned.

(60) Provisional application No. 62/173,874, filed on Jun. 10, 2015.

(51) Int. Cl.

| | |
|---|---|
| ***A61B 18/14*** | (2006.01) |
| ***A61N 1/44*** | (2006.01) |
| *A61B 18/00* | (2006.01) |

(52) U.S. Cl.

CPC ...... *A61N 1/44* (2013.01); *A61B 2018/00517* (2013.01); *H05H 2245/32* (2021.05); *H05H 2245/34* (2021.05)

(58) Field of Classification Search

CPC ........ A61B 2018/00517; A61B 18/042; A61N 1/44; H05H 2245/32; H05H 2245/34

See application file for complete search history.

(56) References Cited

U.S. PATENT DOCUMENTS

| | | | | |
|---|---|---|---|---|
| 3,434,476 A * | 3/1969 | Shaw | A61B 18/042 | 606/22 |
| 6,039,736 A * | 3/2000 | Platt, Jr. | A61B 18/042 | 606/49 |
| 6,099,523 A * | 8/2000 | Kim | A61B 18/1492 | 606/49 |
| 6,517,534 B1 * | 2/2003 | McGovern | A61B 18/1485 | 606/41 |
| 2003/0105458 A1 * | 6/2003 | Platt | A61B 18/042 | 606/49 |
| 2009/0054896 A1 * | 2/2009 | Fridman | A61B 18/042 | 606/49 |
| 2011/0022043 A1 * | 1/2011 | Wandke | H05H 1/2406 | 606/41 |
| 2012/0289954 A1 * | 11/2012 | Lam | A61B 17/3207 | 606/33 |
| 2013/0006229 A1 * | 1/2013 | Delaney | A61B 18/042 | 606/41 |

* cited by examiner

*Primary Examiner* — Jaymi E Della
(74) *Attorney, Agent, or Firm* — Ballard Spahr LLP

(57) ABSTRACT

A system including an internal cold plasma system, including an internal cold plasma applicator configured to couple to a surface surrounding a cavity and to produce a cold plasma between the internal cold plasma applicator and the surface.

20 Claims, 5 Drawing Sheets

48
56
40
88
86
56
88
56
88
58
10

14
78
84
44
80
46
82
50
52
78
16
12
18
54
20
22
46
112
98
14
100
52
106
102
104
111
6
6
110
54
108
12
20
22
16

INTERNAL COLD PLASMA SYSTEM

CROSS-REFERENCE TO RELATED APPLICATION

This application is a divisional application of U.S. patent application Ser. No. 15/177,188, filed Jun. 8, 2016, now abandoned, which claims priority to and benefit of U.S. Provisional Application No. 62/173,874 entitled "Internal Cold Plasma System," filed on Jun. 10, 2015, each of which is hereby incorporated by reference in its entirety.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Modern medical systems enable physicians and veterinarians to treat a wide variety of human and animal ailments. For example, physicians and veterinarians may treat internal ailments using medication, surgery, and radiation. Unfortunately, some of these treatments may have undesirable side effects, long recovery times, etc.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention.

In a first embodiment, a system includes an internal cold plasma system, including an internal cold plasma applicator configured to couple to a surface surrounding a cavity and to produce a cold plasma between the internal cold plasma applicator and the surface.

In a second embodiment, a system includes an internal cold plasma system, which includes an internal cold plasma applicator configured to couple to a surface surrounding a cavity and to produce a cold plasma between the internal cold plasma applicator and the surface. The internal cold plasma system also includes a controller coupled to the internal cold plasma applicator and configured to produce an electrical signal that forms the cold plasma with the internal cold plasma applicator.

In a third embodiment, a method includes production an electrical signal with a controller, and generating a cold plasma using the electrical signal with an internal cold plasma applicator configured to couple to a surface surround a cavity.

BRIEF DESCRIPTION OF THE DRAWINGS

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include an internal cold plasma system capable of forming a non-thermal plasma for treating internal wounds (e.g., pain management, blood coagulation), infections (e.g., bacteria, viruses, yeast, fungi, parasites etc.), cancers (e.g., bladder, cervical, prostate, etc.), tumors, and other conditions. The internal cold plasma system includes an internal cold plasma applicator (e.g., internal treatment cold plasma applicator, insertable cold plasma applicator) that enables the system to treat sites/areas within patient cavities or other hard to reach places. For example, the internal cold plasma applicator may be in the form of a conduit (e.g., catheter). The internal cold plasma applicator may also be sized for use in different animal and human cavities (e.g., sinus cavity, ear canal, anal cavity, urethra, bladder, etc.) enabling more effective treatments of internal ailments or conditions. In some embodiments, the internal cold plasma applicator may be sized to disinfect or sanitize equipment (e.g., medical equipment) that are sensitive to chemicals, heat, or otherwise have hard to reach locations. For example, the internal cold plasma system may be used to disinfect difficult to reach cavities and crevices in a piece of equipment that would involve significant effort or disassembly to reach.

Figure 1:
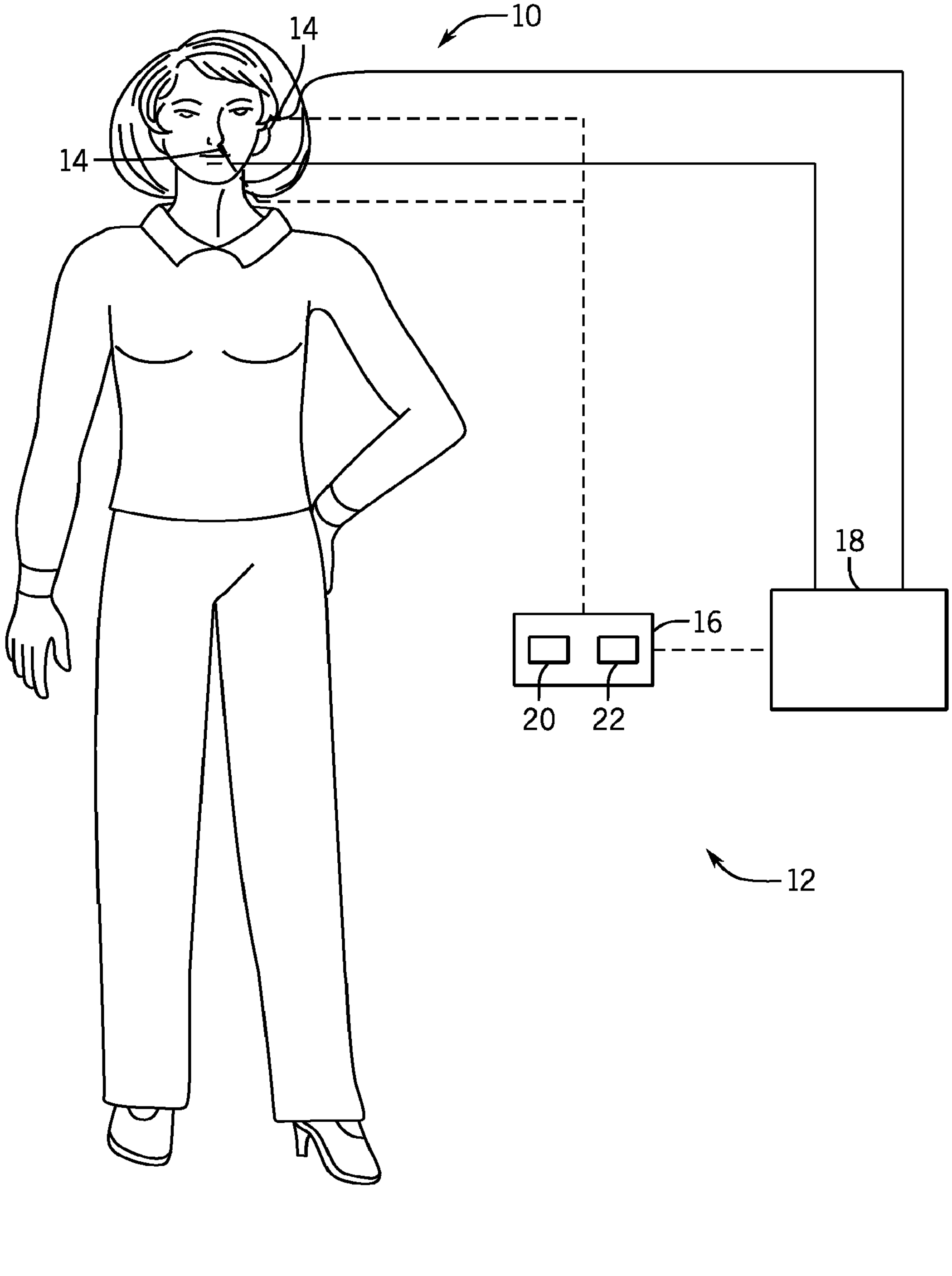
FIG. 1 is an embodiment of an internal cold plasma system coupled to a patient.

FIG. 1 is an embodiment of a patient 10 coupled to an internal cold plasma system 12. The internal cold plasma system 12 may include an internal cold plasma applicator 14, a controller 16, and a gas source 18. As explained above, the internal cold plasma applicator 14 may be in the form of a conduit that facilitates attachment to a patient 10. In operation, the internal cold plasma applicator 14 may convert gas from the gas source 18 or atmospheric gases within the patient 10 into cold plasma (e.g., between the internal cold plasma applicator 14 and a cavity wall).

In order to generate cold plasma, the internal cold plasma system includes a controller 16 with a processor 20 that executes instructions stored on a memory 22. For example, the memory 22 may store instructions for controlling the release and flow of gas from the gas source 18 and for controlling a cold plasma-generating electrical signal (e.g., change power; amplitude; frequency or frequencies; pulse timing; etc.). The electrical signal may be a multi-frequency, harmonic-rich signal (e.g., a timed pulse electrical signal that is pulsed between 100-1000 Hz with an output voltage between 1-100 kV having multiple A/C waves at multiple frequencies that overlap to produce 2-2,000,000 or more harmonic components between DC and 500 MHz). As the multi-frequency, harmonic-rich electrical signal passes through the gas (e.g., gas from the gas source 18 or atmospheric gases); the gas molecules/atoms lose and gain electrons to produce cold plasma with positive ions, negative ions, and electrons. It is believed that the multi-frequency, harmonic-rich electrical signal facilitates removal of electrons from molecules/atoms with less energy than typical plasma formation. Accordingly, the plasma is a low temperature plasma or cold plasma (e.g., a cold plasma with a temperature between approximately 60-120, 60-80, 70-90, 80-100, 90-110, 100-120 degrees Fahrenheit), enabling exposure to a temperature sensitive target substrate (e.g., biological tissue).

Figure 2:
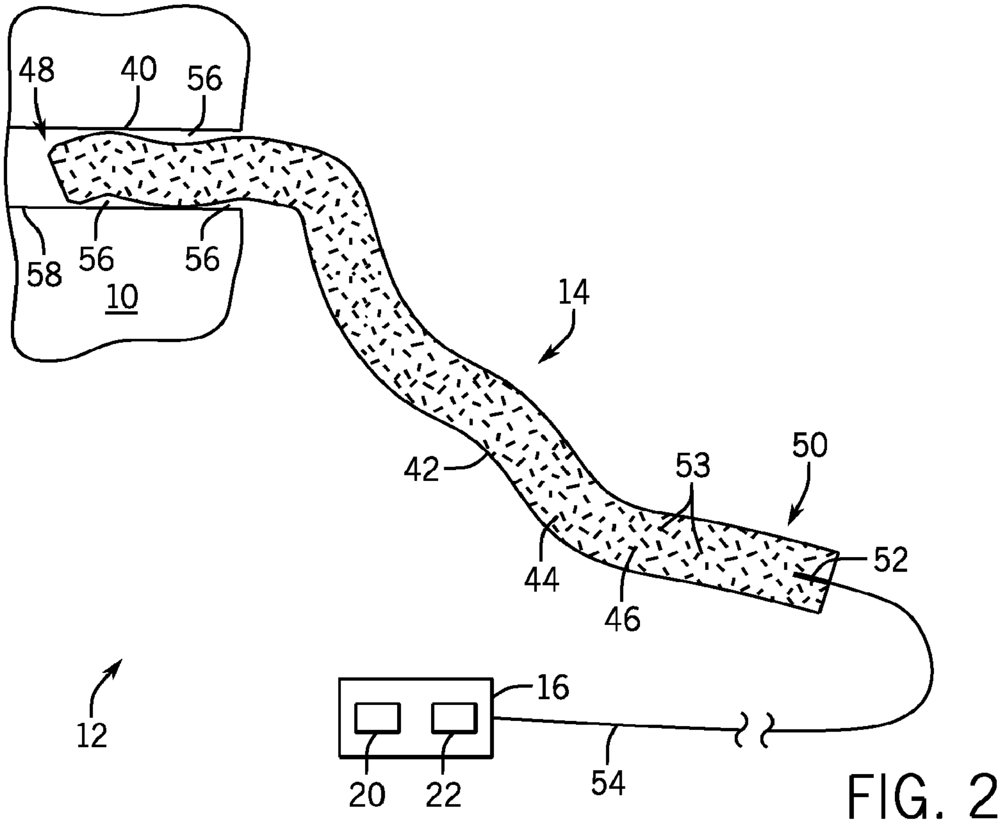
FIG. 2 is a cross-sectional view of an embodiment of an internal cold plasma system partially inserted into a cavity.

FIG. 2 is a cross-sectional view of an embodiment of an internal cold plasma system 12 with an internal cold plasma applicator 14 partially inserted into a cavity 40. The cavity 40 may be in an animal, human, or equipment. Some animal and human cavities 40 may include a sinus cavity, ear canal, anal cavity, urethra, bladder, etc. As illustrated, the internal cold plasma applicator 14 includes a conduit 42 (e.g., catheter) with a cavity 44 (e.g., passage, lumen, elongated chamber) that contains a conductive fluid, gas, or gel/hydrogel 46. The conduit 42 may be made out of a rigid, semi-rigid, or flexible dielectric material that enables a user to insert the conduit 42 into a variety of cavities 40. For example, the conduit 42 may be made out of a silicone, latex, hydrogels, polyoxymethylene, polyamide, polytetrafluoroethylene (PTFE), acetal homopolymer, polyethylene (PE), polypropylene (PP), poly vinyl chloride (PVC), ethylene vinyl acetate (EVA), propylene, copolyester ether, and polyolefin film. In embodiments where the conduit 42 is flexible, the flexibility of the conduit 42 enables the internal cold plasma applicator 14 to conform to different cavities 40 on a variety of patients 10. The conduit 42 may also be formed in a variety of cross-sectional shapes that conform to a passageway or cavity 40 (e.g., oval, circular, irregular, crescent, etc.).

In some embodiments, a first end 48 of the conduit 42 may be tapered to facilitate alignment and insertion into a cavity 40 while the second end 50 receives an electrode 52. The electrode 52 extends through the conduit 42 and into contact with the conductive fluid 46 (e.g., saline, potassium, chlorine, etc.). The fluid 46 may be a multi-phase fluid (e.g., gas, gel/hydrogel and/or liquid) that includes conductive material 53 (e.g., dissolved salts, carbon, metals, etc.). In operation, the electrical signal from the controller 16 passes through a cable 54 (e.g., HV/RF feed cables) to the electrode 52 and into the conductive fluid 46. The conductive fluid 46 then conducts the electric signal through the cavity 44 (e.g., lumen) toward a surface of lower electrical potential (e.g., the patient 10). As explained above, the conduit 42 is made out of a dielectric material. The dielectric material enables the electrical signal to build charge inside the conduit 42. Once a sufficient amount of charge builds, the electrical signal crosses through the dielectric material of the conduit 42 and gaps 56 to the patient's skin (e.g., surface of lower electrical potential). As the electrical signal crosses through the gaps 56, the electrical signal forms cold plasma by ionizing atmospheric gases. In other words, the electrical signal enables atmospheric gas molecules/atoms to lose and gain electrons to produce the cold plasma with positive ions, negative ions, and electrons. As the internal cold plasma applicator 14 is inserted further and/or rotated within the cavity 40, the gaps 56 may change position and change size enabling cold plasma treatment of the entire or a substantial portion of the internal surface/walls 58 of the cavity 40. In some embodiments, the atmospheric gases may form certain ions when converted into a cold plasma. These ions may be ideally suited for killing bacteria or to promote faster healing (e.g., combinations of helium, oxygen, OH ions).

Figure 3:
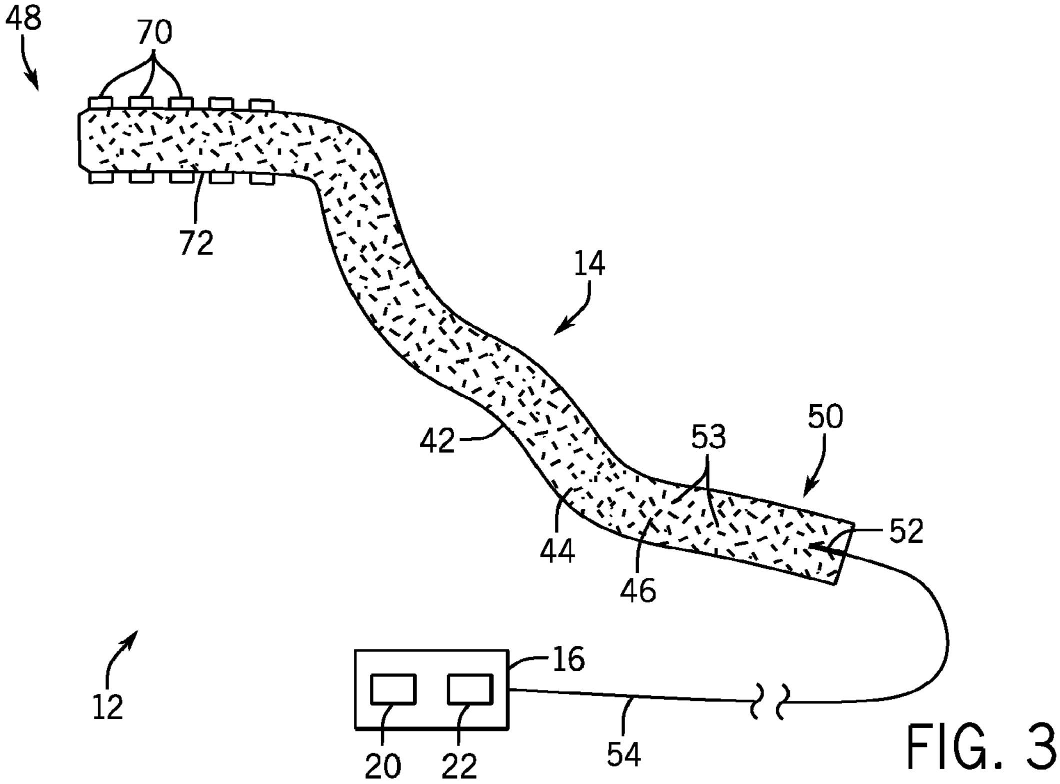
FIG. 3 is a cross-sectional view of an embodiment of an internal cold plasma system.

FIG. 3 is a cross-sectional view of an embodiment of an internal cold plasma system 12 with an internal cold plasma applicator 14. Like the internal cold plasma applicator 14 in FIG. 2, the internal cold plasma applicator 14 in FIG. 3 includes a conduit 42 with a cavity 44 (e.g., lumen) that enables the internal cold plasma applicator 14 to receive a conductive fluid 46. However, to facilitate cold plasma formation within a cavity 40 (e.g., bodily or internal cavity of target), the internal cold plasma applicator 14 may include a plurality of spacers 70 (e.g., ridges) along an outer surface 72 of the conduit 42. The internal cold plasma applicator 14 may include these spacers 70 along a portion or about the entire outer surface 72 of the conduit 42. In operation, the spacers 70 create distance between the outer conduit surface 72 and the interior surface/walls 58 of the cavity 40 enabling gas (e.g., atmospheric gases) to substantially surround the conduit 42 for cold plasma generation. In some embodiments, the spacers 70 may be uniform in height and/or spacing. In other embodiments, the height of the spacers 70 and/or space between the spacers 70 may vary. Furthermore, the spacers 70 may extend completely around the conduit 42, extend partially around the conduit 42, or a combination thereof.

Figure 4:
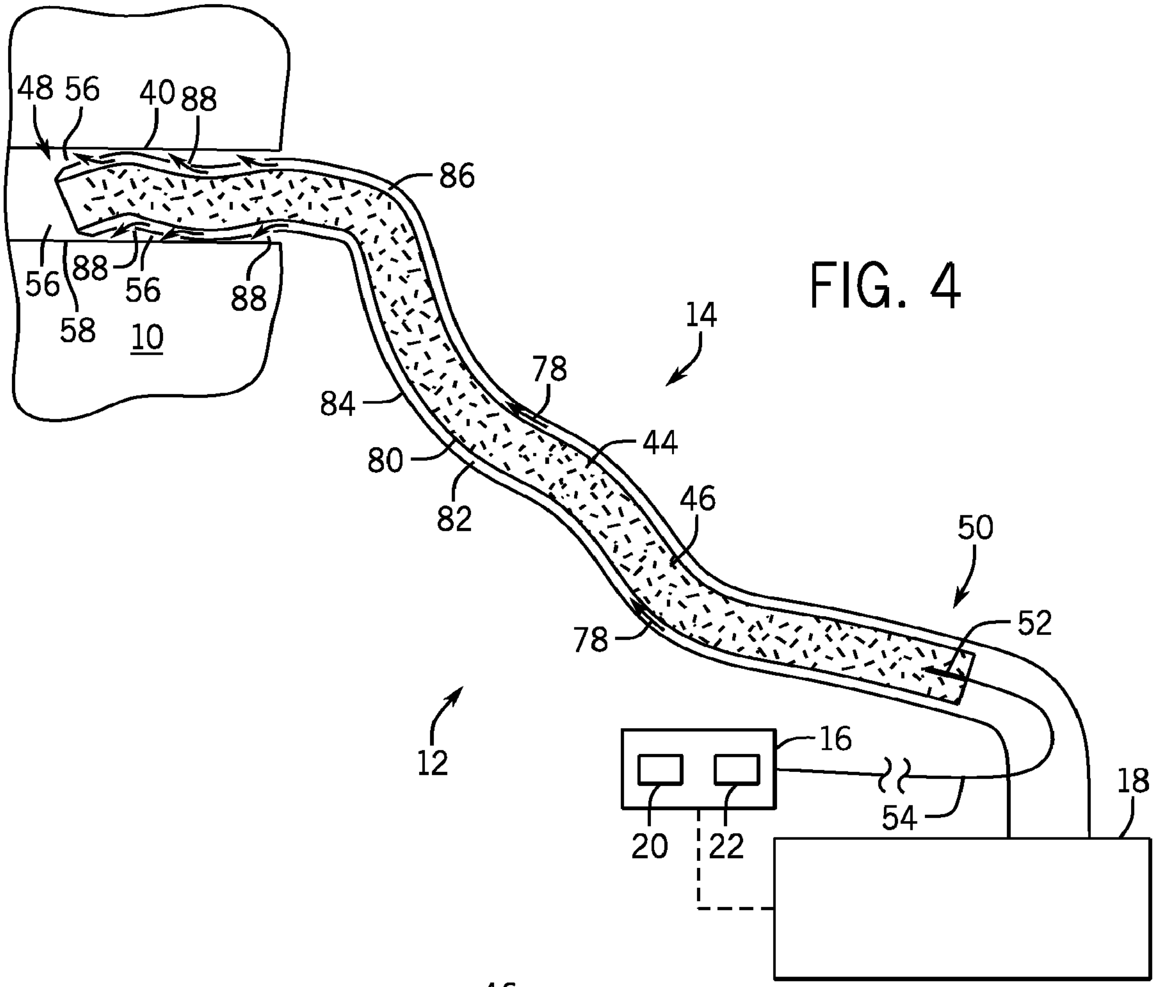
FIG. 4 is a cross-sectional view of an embodiment of an internal cold plasma system partially inserted into a cavity.

FIG. 4 is a cross-sectional view of an embodiment of an internal cold plasma system 12 with an internal cold plasma applicator 14 partially inserted into a cavity 40 (e.g., bodily or internal cavity of target). In operation, the internal cold plasma applicator 14 delivers a gas 78 from a gas source 18 into the cavity 40. The internal cold plasma applicator 14 then converts the gas 78 into a cold plasma. In some embodiments, the gas 78 may be a specialized gas that forms certain ions when converted into a cold plasma. These ions may be ideally suited for killing bacteria or to promote faster healing (e.g., combinations of helium, oxygen, OH ions). For example, the gas 78 may be a single gas or a mixture of gases (e.g., helium, neon, argon, krypton, xenon, radon, oxygen, nitrogen, or any combination thereof) that form cold plasmas with different properties suited for specific treatments (e.g., a gas that promotes faster wound healing, blood coagulation, infection treatment, etc.).

In order to conduct the gas 78, the internal cold plasma applicator 14 includes an inner conduit 80 that rests within a cavity 82 (e.g., passage, lumen) of an outer conduit 84. Together, the inner and outer conduits 80, 84 form a gap 86 (e.g., annular gap) that enables gas 78, from the gas source 18, to flow through the outer conduit 84 and around the inner conduit 80 to a first end 48 of the internal cold plasma applicator 14. As the gas 78 reaches the first end 48, the gas 78 exits the outer conduit 84 through apertures 88 (e.g., circumferentially spaced, axially spaced, or a combination thereof) and into the gaps 56. As the gas 78 exits through the apertures 88, the internal cold plasma applicator 14 converts the gas 78 into a cold plasma. In some embodiments, the first end 48 may also be tapered to facilitate alignment and insertion into a cavity 40. For example, the first end 48 may be frustoconical or have a curved annular shape (e.g., ball shaped, bulb shaped).

As illustrated, the inner conduit 80 includes a conductive fluid 46 and an electrode 52 within the cavity 44 (e.g., lumen). As explained above, the conductive fluid 46 may be a multi-phase fluid (e.g., gas and/or liquid) that includes conductive material 53 (e.g., dissolved salts). In operation, the electrical signal from the controller 16 passes through the cable 54 (e.g., HV/RF feed cables) to the electrode 52 and into the conductive fluid 46. The conductive fluid 46 then conducts the electric signal through the inner conduit 80 toward ground (e.g., the patient 10). The inner conduit 80 is made out of a dielectric material that enables the electrical signal to build charge inside the inner conduit 80. After building enough charge, the electrical signal crosses through the dielectric material of the inner conduit 80 and through the gas 78 in the gaps 56 to the patient's skin (e.g., ground). As the electrical signal crosses through the gas 78 to ground, the electrical signal converts the gas 78 into a cold plasma. In other words, the electrical signal enables the molecules/atoms in the gas 78 to lose and gain electrons to produce cold plasma with positive ions, negative ions, and electrons. As the internal cold plasma applicator 14 is inserted further and/or rotated within the cavity 40, the gaps 56 may change size and/or position enabling the entire or a substantial portion of the cavity 40 to be treated with cold plasma. In some embodiments, the outer conduit 84 may include spacers 70, as shown in FIG. 3 and discussed above, that create distance between the outer conduit 84 and the cavity 40 enabling the gas 78 to substantially surround the outer conduit 84 during plasma generation.

The inner and outer conduits 80, 84 may be made out of a rigid, semi-rigid, or flexible dielectric material that enables a user to insert the conduits 80, 84 into a variety of cavities 40. For example, the conduits 80, 84 may be made out of a silicone, latex, hydrogels, polyoxymethylene, polyamide, polytetrafluoroethylene (PTFE), acetal homopolymer, polyethylene (PE), polypropylene (PP), poly vinyl chloride (PVC), ethylene vinyl acetate (EVA), propylene, copolyester ether, and polyolefin film. In embodiments where the conduits 80, 84 are flexible, the flexibility of the conduits 80, 84 enable the internal cold plasma applicator 14 to conform to different cavities 40 on a variety of patients.

Figure 5:
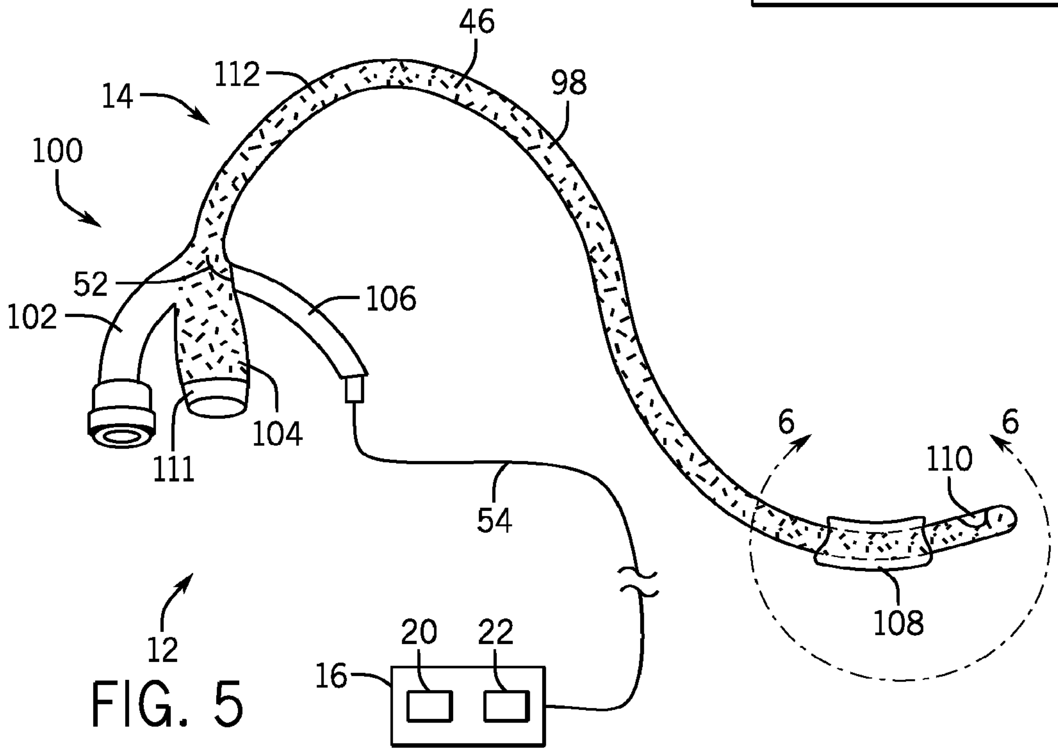
FIG. 5 is a perspective view of an embodiment of an internal cold plasma system.

FIG. 5 is a cross-sectional view of an embodiment of an internal cold plasma system 12 with an internal cold plasma applicator 14. As illustrated, the internal cold plasma applicator 14 includes a conduit 98 that branches into secondary conduits 100. While FIG. 5 shows three secondary conduits 100, other embodiments may include different numbers of secondary conduits 100 (e.g., 1, 2, 3, 4, 5, or more). For example, the internal cold plasma applicator 14 may include a fluid conduit 102 (e.g., balloon port), a fluid drainage conduit 104, and an electrode conduit 106. In operation, the fluid conduit 102 enables a fluid (e.g., gas or liquid) to be pumped into the internal cold plasma applicator 14 to inflate an inflatable portion 108, wherein the fluid may also be a conductive fluid (e.g., saline, potassium, chlorine, gas, gel/hydrogel, and/or liquid, etc.). For example, the internal cold plasma applicator 14 may be inserted into a cavity 40 and the inflatable portion 108 may be inflated to block removal of the internal cold plasma applicator 14, or to maintain the internal cold plasma applicator 14 in a desired position or location. After insertion, the fluid drainage conduit 104 enables fluid to enter or exit the patient 10 through an opening 110 in the conduit 98. For example, the internal cold plasma applicator 14 may facilitate the draining of bodily fluids (e.g., urine, blood, etc.) from the patient 10 or injecting fluid into the patient 10 (e.g., medicine, saline, etc.). In some embodiments, fluid flow into and out of the fluid drainage conduit 104 may be controlled with a valve or plug 111. Moreover, in some embodiments, the internal cold plasma applicator 14 may include additional openings 110 (e.g., 1, 2, 3, 4, 5, or more). Furthermore, there may be a valve disposed at any of the opening(s) 110, and the valve may be controlled via the controller 16 such that upon receiving a signal from the controller 16, the valve may be actuated to an open or closed position to open or close the openings (110). For example, after the draining of bodily fluids (e.g., urine, blood, etc.) from the patient 10, the opening 110 may be closed.

As explained above, the internal cold plasma applicator 14 enables internal treatment of a patient 10 with cold plasma. To facilitate production of cold plasma, the internal cold plasma applicator 14 includes the electrode conduit 106. The electrode conduit 106 enables an electrode 52 electrically coupled to the controller 16 to communicate with the cavity 112. In some embodiments, the internal cold plasma applicator 14 may not include the electrode conduit 106. Instead, the electrode 52 may extend through an aperture in the conduit 98 or the fluid drainage conduit 104. In operation, the electrical signal from the controller 16 passes through the cable 54 (e.g., HV/RF feed cables) to the electrode 52 and into a conductive fluid 46 within the internal cold plasma applicator 14. The conductive fluid 46 may be a conductive bodily fluid (e.g., urine, blood, etc.) from the patient 10 or another conductive fluid (e.g., medicine, saline, etc.) that is injected into the patient 10. The conductive fluid 46 then conducts the electric signal through the cavity 112 (e.g., lumen) toward ground (e.g., the patient).

The conduit 98 and fluid drainage conduit 104 may be made out of a dielectric material. As explained above, dielectric material enables an electrical signal to build charge. Accordingly, once enough charge builds, the electrical signal crosses through the dielectric material of the conduit 98 and through a gas (e.g., atmospheric gases) to ground (e.g., patient's skin). As the electrical signal passes through the gas, the electrical signal forms cold plasma. In some embodiments, the conduit 98 may include spacers (e.g., spacers 70 shown in FIG. 3) that maintain a gap between the conduit 98 and a cavity 40 enabling gas (e.g., atmospheric gases) to substantially surround the conduit 98 within a cavity 40. In some embodiments, the conduit 98 and conduit 102 may include an outer conduit surrounding the conduit 98 and conduit 102 forming a gap (e.g., inner conduit 80, outer conduit 84 without apertures 88, and gap 86 shown in FIG. 4) that enables gas (e.g., gas 78 from gas source 18 shown in FIG. 4) or conductive fluid to flow through the outer conduit and around the inner conduit as discussed below in FIGS. 8 and 9.

Figure 6:
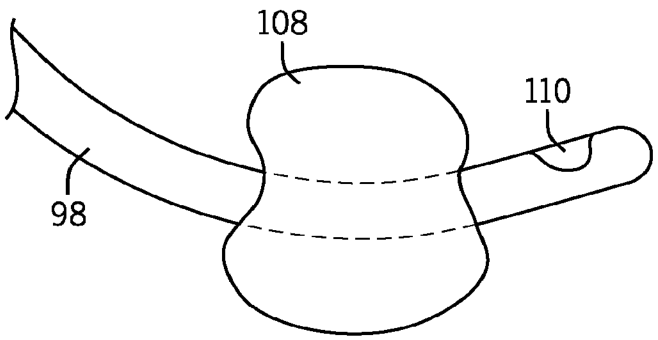
FIG. 6 is a sectional view of an embodiment of an internal cold plasma applicator within lines 6-6 of FIG. 5.

FIG. 6 is a sectional view of an embodiment of the internal cold plasma applicator 14 within line 6-6 of FIG. 5. As explained above, the internal cold plasma applicator 14 may include an inflatable portion 108 (e.g., balloon) that that receives fluid from the fluid conduit 102. In operation, the inflatable portion 108 may be inflated to block removal of the internal cold plasma applicator 14, or to maintain the internal cold plasma applicator 14 in a desired position or location. In some embodiments, the inflatable portion 108 may cover the opening 110 when inflated. For example, when inflated, the inflatable portion 108 may be used to block fluid flow into a patient 10 and/or block fluid flow out of a patient 10 (e.g., urine). In some embodiments, the inflatable portion 108 may expand in response to mechanical actuation. In some embodiments, the opening 110 may remain opened or closed position in response to mechanical actuation.

Figure 7:
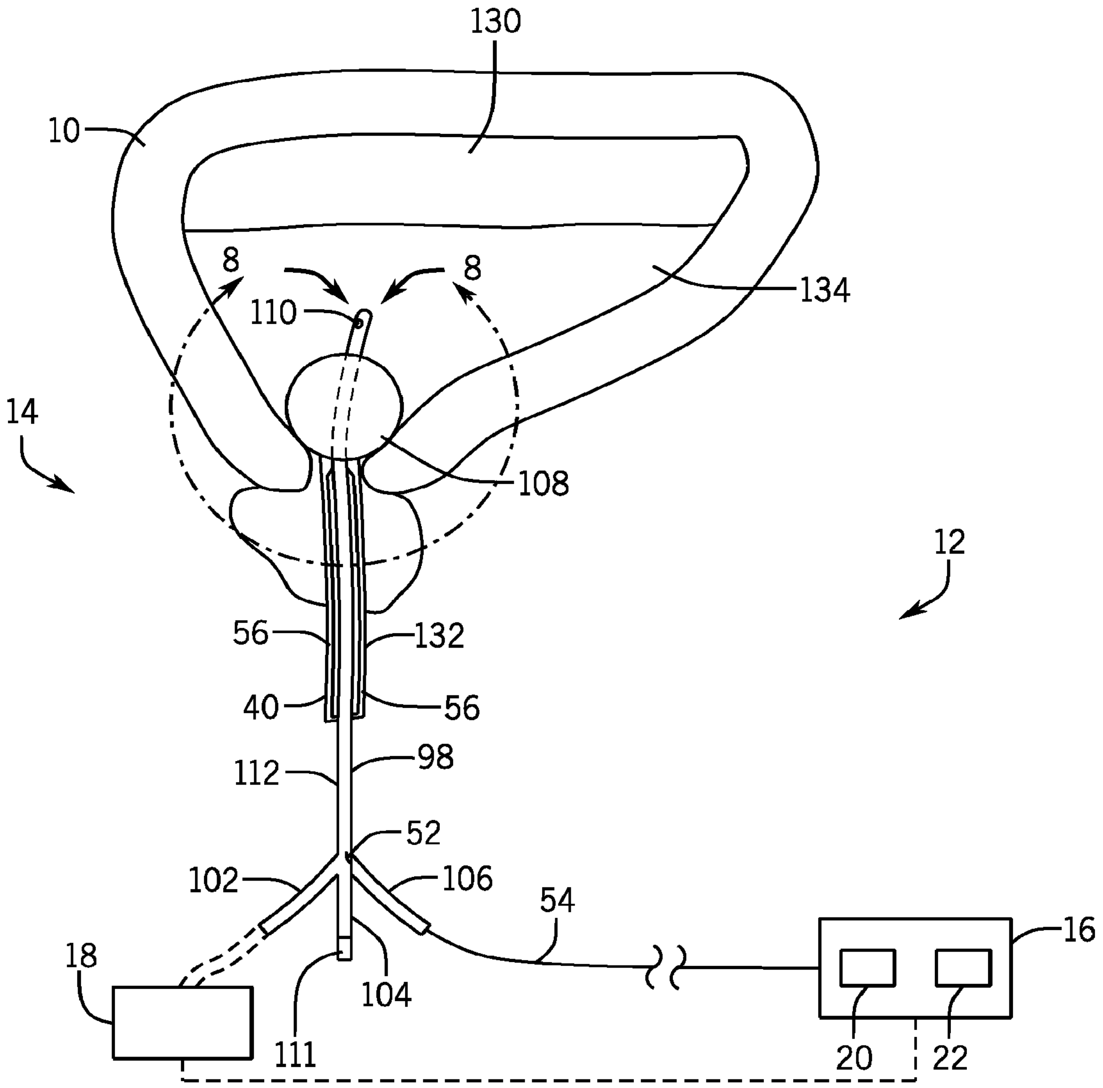
FIG. 7 is a side view of an embodiment of an internal cold plasma system coupled to patient.

FIG. 7 is a side view of an embodiment of the internal cold plasma system 12 with an internal cold plasma applicator 14 coupled to a patient 10. As illustrated, the conduit 98 of the internal cold plasma applicator 14 may be inserted into a cavity 130 (e.g., bladder) of the patient 10 through a passageway 132 (e.g., urethra). Once inside the cavity 130, the inflatable portion 108 may be inflated to retain the internal cold plasma applicator 14 in position. A conductive fluid 134 may then be drained or pumped into the cavity 130 through the opening 110 in the conduit 98. For example, a patient's bladder may be drained in order to generate cold plasma within the bladder and urethra.

After draining or filling the conduit 98, an operator may stop the flow of conductive fluid 134 through the fluid drainage conduit 104 with the valve or plug 111, to retain the conductive fluid 134 within the conduit 98. Once the conduit 98 fills with the conductive fluid 134, the internal cold plasma applicator 14 is able to conduct the electric signal toward ground (e.g., the patient 10). The conduit 98 and fluid drainage conduit 104 may be made out of a dielectric material. As explained above, dielectric material enables the electrical signal to build charge within the conduit 98. After building a sufficient amount of charge, the electrical signal crosses the dielectric material and through a gas (e.g., atmospheric gases in the gaps 56) to the patient's tissue(s) (e.g., ground). As the electrical signal crosses through the gas containing gaps 56, the internal cold plasma applicator 14 forms cold plasma in the passageway 132 and/or within the cavity 130. In some embodiments, the internal cold plasma applicator 14 may be further inserted, rotated, etc. to change the position of the gas containing gaps 56 enabling treatment of all or a substantial portion of the passageway 132 and cavity 130. The natural or normal movement of the patient 10 may also move the internal cold plasma applicator 14, which changes the size and/or position of the gaps 56 enabling treatment of all or a substantial portion of the passageway 132 and cavity 130.

Figure 8:
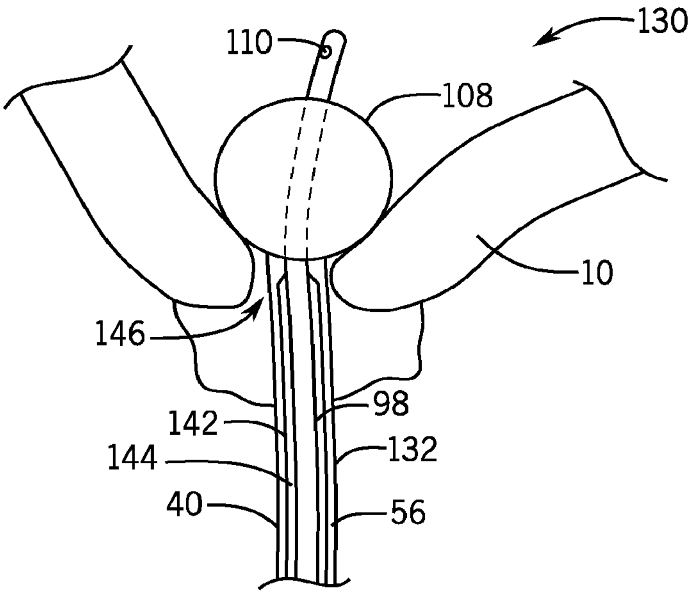
FIG. 8 is a sectional view of an embodiment of an internal cold plasma applicator within lines 8-8 of FIG. 7.
Figure 9:
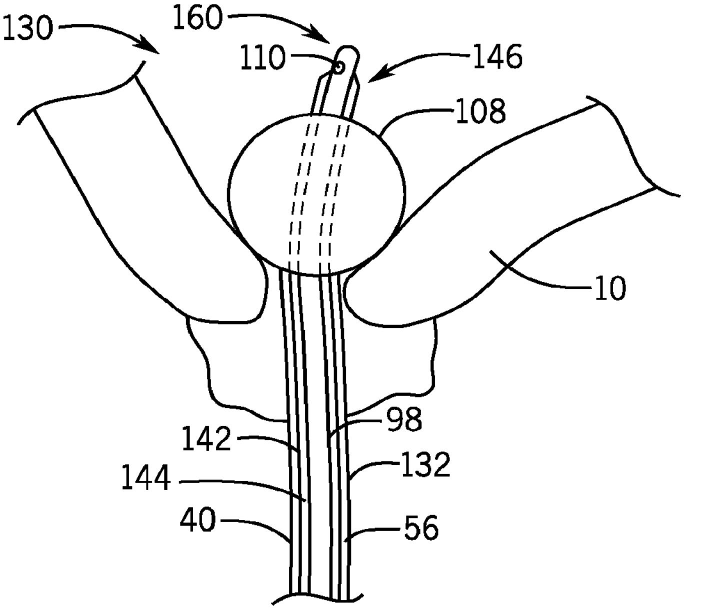
FIG. 9 is another embodiment of a section of an internal cold plasma applicator of FIG. 8.

FIGS. 8 and 9 are sectional views of embodiments of an internal cold plasma applicator 14 within line 8-8 of FIG. 7. As illustrated in FIGS. 8 and 9, the conduit 98 (e.g., inner conduit) rests within or extends through an outer conduit 142. In other words, the conduits 142 and 98 may be disposed one around another in a coaxial or concentric arrangement to define an intermediate passage or gap 144 (e.g., annular passage or gap). The passage 144 enables a fluid flow between the conduits 142 and 98. In the embodiment of FIG. 8, the outer conduit 142 couples to the inflatable portion 108 but does not extend completely through the inflatable portion 108, while the inner conduit 98 couples to and extends completely through the inflatable portion 108 and protrudes away from the inflatable portion 108 into the cavity 130. In the embodiment of FIG. 9, both the inner conduit 98 and the outer conduit 142 couple to and extend completely through the inflatable portion 108. In particular, the inner conduit 98 and the outer conduit 142 both protrude away from the inflatable portion 108 and into the cavity 130, while the end 160 of the inner conduit 98 is offset further downstream from the end 146 of the outer conduit 142.

In some embodiments of the system 12 shown in FIGS. 8 and 9, the cavity 130 may be drained of bodily fluids (e.g., urine, blood, etc.) through one or more drainage conduits, such as the inner conduit 98 (e.g., via opening 130), the outer conduit 42, or another drainage conduit. Subsequently, the drainage conduit (e.g., opening 110 in the inner conduit 98) may be closed via a valve or the drainage conduit may remain open. In certain embodiments, the inner conduit 98 may be configured to hold and/or flow a conductive fluid (e.g., liquid, gel such as hydrogel, and/or gas), while the outer conduit 142 (e.g., in passage 144) may be configured as a dielectric (e.g., either empty or filled with a dielectric material). Alternatively, the outer conduit 142 (e.g., in passage 144) may be configured to hold and/or flow a conductive fluid (e.g., liquid, gel such as hydrogel, and/or gas), while the inner conduit 98 may be configured as a dielectric (e.g., either empty or filled with a dielectric material). For example, embodiments using one of the conduits (e.g., 98 or 142) as a dielectric may fill the conduit with a dielectric material (e.g., liquid, gas, and/or solid), or the conduit may be empty of one or more of liquids, gases, and/or solids (e.g., vacuum void of matter or substantially void of matter). In some embodiments, the system 12 may include 1, 2, 3, 4, 5, or more additional conduits extending along the conduits 98 and 142 in a side by side configuration, one about another in a coaxial or concentric configuration, or a combination thereof. The various conduits may be used for fluid injection, fluid drainage, dielectric materials, conductive fluids, monitoring via cameras, sensors, or probes, or any combination thereof.

As explained above with reference to FIG. 7, as the electrical charge builds up and crosses through the gas containing gap 56 between the outer conduit 142 and the passageway 132, the internal cold plasma applicator 14 forms cold plasma in the passageway 132. In applications with the conductive fluid 134 drained from the cavity 130, the cold plasma may form primarily within the passageway 132 (e.g., in the embodiment of FIG. 8), although the cold plasma also may form partially, substantially, or completely inside of the cavity 130. Accordingly, the cold plasma treatment may be focused primarily on the passageway 132 rather than the cavity 130 in some embodiments. In some embodiments, the inflatable portion 108 may be filled with conductive fluid (e.g., liquid, gel such as hydrogel, and/or gas) such that cold plasma can also form around the inflatable portion 108 (e.g., using the drained cavity 130 as dielectric), enabling cold plasma treatment of at least a portion of the cavity 130 of the patient 10. However, the internal cold plasma applicator 14 may be configured to selectively provide cold plasma treatment of any specific area of interest in the passageway 132, the cavity 130, or a combination thereof.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An internal cold plasma system comprising:

an applicator configured to be disposed within a cavity of a patient and to produce a cold plasma only between an outer surface of the applicator and a surface of the patient, wherein the applicator is configured to be navigated through an anatomical passage of the patient into the cavity of the patient, wherein the applicator comprises a flexible conduit configured to enable the applicator to conform to different cavities of different patients, wherein the flexible conduit has a first passage extending between a first end and a second end, wherein the first passage contains a conductive fluid, wherein the flexible conduit is defined by a wall made of a dielectric material, and wherein the dielectric material is configured to enable an electrical signal to build charge inside the flexible conduit, wherein the applicator further comprises a second conduit having a second passage, wherein the second passage is configured to function as a dielectric by carrying additional dielectric material or being empty, and wherein the applicator further comprises a plurality of apertures arranged about a circumference of the outer surface of the applicator, wherein each aperture of the plurality of apertures is in communication with the second passage.

2. The system of claim 1, wherein the applicator is a catheter that is configured to be inserted into a urethra of the patient.

3. The system of claim 1, wherein the dielectric material of the wall of the flexible conduit is configured to enable the electrical signal to build the charge inside the flexible conduit until a sufficient amount of charge builds whereupon the electrical signal crosses through the wall between the first end and the second end and produces the cold plasma from fluid within a gap between the wall and the surface of the patient.

4. The system of claim 1, wherein the second conduit surrounds the flexible conduit, and the second passage is disposed between the flexible conduit and the second conduit.

5. The system of claim 3, further comprising an electrode that rests within the first passage.

6. The system of claim 3, wherein the first end of the flexible conduit comprises a tapered end that facilitates insertion into the cavity of the patient.

7. The system of claim 1, further comprising a plurality of spacers configured to separate a cold plasma-generating surface of the flexible conduit from the surface of the patient.

8. The system of claim 1, further comprising a controller configured to produce the electrical signal that forms the cold plasma with the applicator from fluid within a gap between the outer surface of the applicator and the surface of the patient.

9. The system of claim 2, wherein the flexible conduit comprises an inflatable portion, wherein the inflatable portion is configured to block retraction and enable secure placement of the catheter after insertion into the urethra of the patient.

10. The system of claim 3, wherein the applicator is configured to use the conductive fluid to carry the electrical signal that generates the cold plasma.

11. A method comprising:

positioning the applicator of the system of claim 8 within the cavity of the patient;

producing the electrical signal with the controller, and generating the cold plasma using the electrical signal, wherein the conductive fluid conducts the electrical signal toward the patient.

12. The method of claim 11, further comprising pumping a gas from a gas source to the applicator.

13. The method of claim 11, wherein the conductive fluid is a conductive bodily fluid of the patient.

14. The method of claim 13, wherein the conductive bodily fluid is urine.

15. The method of claim 11, wherein the conductive fluid comprises saline.

16. The method of claim 11, wherein the applicator of the system is a catheter, and wherein the applicator is positioned within a urethra the anatomical passage of the patient, wherein the anatomical passage is a urethra of the patient.

17. The method of claim 16, wherein the conductive fluid is urine of the patient.

18. The method of claim 16, further comprising inflating an inflatable portion of the flexible conduit to block retraction and secure the catheter within the urethra of the patient.

19. An internal cold plasma system comprising:

an applicator configured to be disposed within a cavity of a patient and to produce a cold plasma only between an outer surface of the applicator and a surface of the patient, wherein the applicator is configured to be navigated through an anatomical passage of the patient into the cavity of the patient, wherein the applicator comprises a flexible conduit configured to enable the applicator to conform to different cavities of different patients, wherein the flexible conduit has a first passage extending between a first end and a second end, wherein the first passage contains a conductive fluid, wherein the flexible conduit is defined by a wall made of a dielectric material, and wherein the dielectric material is configured to enable an electrical signal to build charge inside the flexible conduit, wherein the applicator further comprises a second conduit having a second passage, wherein the second passage is configured to function as a dielectric by carrying additional dielectric material or being empty, and wherein the flexible conduit surrounds the second conduit, and wherein the first passage is disposed between the flexible conduit and the second conduit.

20. The internal cold plasma system of claim 1, wherein the plurality of apertures comprises a first aperture and a second aperture that is circumferentially spaced from the first aperture about the outer surface of the applicator.

* * * * *